(12) United States Patent
Yue et al.

(10) Patent No.: US 6,344,456 B1
(45) Date of Patent: Feb. 5, 2002

(54) PIPERAZINONE DERIVATIVES AND THEIR USES

(75) Inventors: Christophe Yue; Marguerite Henry, both of Maisons Alfort; Thierry Giboulot, Vincennes; Brigitte Lesur, Champs-sur-Marne, all of (FR)

(73) Assignee: Laboratoire L. Lafon, Maisons Alfort (FR)

( * ) Notice: Subject to any disclaimer, the term of this patent is extended or adjusted under 35 U.S.C. 154(b) by 0 days.

(21) Appl. No.: 09/743,411

(22) PCT Filed: Jul. 16, 1999

(86) PCT No.: PCT/FR99/01747

§ 371 Date: Jan. 10, 2001

§ 102(e) Date: Jan. 10, 2001

(87) PCT Pub. No.: WO00/04000

PCT Pub. Date: Jan. 27, 2000

(30) Foreign Application Priority Data

Jul. 17, 1998 (FR) .............................. 98/09168

(51) Int. Cl.$^7$ .................. A61K 31/495; A61K 31/496; C07D 241/08; C07D 401/12; C07D 405/12

(52) U.S. Cl. .............................. 514/235.8; 514/252.13; 514/253.01; 514/253.06; 514/253.07; 514/254.11; 514/255.03; 544/121; 544/357; 544/360; 544/363; 544/376; 544/377; 544/379; 544/393

(58) Field of Search .................. 544/377, 393, 544/121, 363, 360, 379, 376, 357; 514/235.8, 255.03, 252.13, 253.01, 253.06, 253.07, 254.11

(56) References Cited

U.S. PATENT DOCUMENTS 5,442,064 A  *  8/1995  Pieper et al. ................ 544/360
5,908,843 A  *  6/1999  Gante et al. ................ 514/255

FOREIGN PATENT DOCUMENTS

EP         0 608 759 A3      8/1994
EP         0 608 759 A2      8/1994

* cited by examiner

*Primary Examiner*—Emily Bernhardt
(74) *Attorney, Agent, or Firm*—Young & Thompson

(57) ABSTRACT

The invention concerns compounds of formula (I)

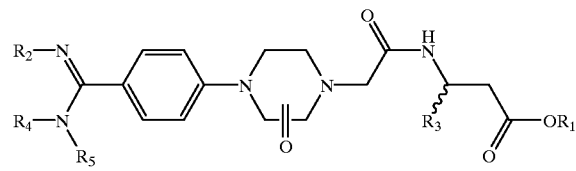

wherein $R_1$, $R_2$, $R_3$, $R_4$ and $R_5$ are as defined herein. Said compounds are useful in therapy as antithrombotic agents.

7 Claims, No Drawings

PIPERAZINONE DERIVATIVES AND THEIR USES

The present invention relates to novel compounds which are inhibitors of the binding of fibrinogen to the Gp IIb/IIIa platelet receptors, and which can be used therapeutically as antithrombotic agents.

In the course of the pathological processes which lead to the formation of a thrombus (clot) and then to its extension, platelet aggregation represents a key step since it is the source of the seriousness of the phenomenon. Specifically, from the initiation of the thrombus, in particular in the arterial blood circulation, the action of several interdependent biochemical reactions induces the aggregation of an increasingly large number of platelets via the conversion of soluble fibrinogen into insoluble fibrin filaments which increase the size of the mass of platelets, first at the actual site of the arterial vascular lesion, and then increasingly in the lumen of the vessel.

In this mechanism of platelet aggregation, activation of the Gp IIb/IIIa receptors is the source of the amplification of the platelet aggregation. Fibrinogen, which can bind via its two dimers to these receptors, amplifies the binding-together of the platelets and thus induces the formation of a platelet mass forming a thrombus at the site of rupture of the atheroma plaque.

This mechanism of platelet aggregation is particularly active in all arterial thromboses, whether they appear in the course of performing interventional cardiology (transluminal percutaneous angioplasty; insertion of stents), heart surgery (aorto-coronary bypass; valve surgery), in the course of acute heart diseases (myocardial infarction, unstable angina, acute coronary syndromes, etc.) or in the course of certain cerebral ischaemias, or finally in the course of myocardial ischaemias which may complicate the follow-up of an antithrombotic treatment.

Reducing or preventing the activation of platelets in contact with a broken atherosclerotic plaque thus represents a novel and effective therapeutic approach to the treatment of thrombosis, in particular arterial thrombosis, and thus an efficient means for preventing acute coronary syndromes, including unstable angina and myocardial infarction.

The present invention is directed towards providing novel competitive inhibitors of the binding of fibrinogen to the Gp IIb/IIIa receptors which can be used as antithrombotic medicines.

The present invention is also directed towards providing compounds which can be administered orally, thus allowing a prolonged duration of action to be obtained and avoiding the risks of bleeding.

One subject of the present invention is compounds of general formula (I):

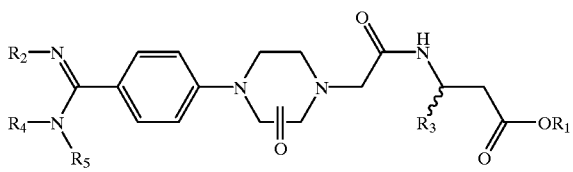

(I)

in which:
$R_1$ is chosen from hydrogen, a $C_1$–$C_4$ alkyl group and a phenyl ($C_1$–$C_4$ alkyl) group;
$R_2$ is chosen from hydrogen, a hydroxyl group and a protecting group for the amidino group;

$R_3$ is chosen from
hydrogen,
$C_1$–$C_5$ alkyl, $C_3$–$C_{12}$ mono- or bicyclic cycloalkyl, $C_2$–$C_4$ alkenyl and $C_2$–$C_4$ alkynyl groups, these groups optionally being substituted with groups chosen from halogens and the hydroxyl group;
mono-, bi- or tricyclic $C_6$–$C_{14}$ aryl groups,
heteroaryl groups chosen from pyridyl, thienyl, furyl, quinolyl, benzodioxanyl, benzodioxolyl, benzothienyl, benzofuryl and pyrazinyl groups;
phenyl ($C_1$–$C_4$) alkyl and napthyl ($C_1$–$C_4$) alkyl groups optionally substituted on the aryl nucleus, and piperonyl groups,
$R_4$ and $R_5$ are chosen, independently of each other, from hydrogen and a $C_1$–$C_5$ alkyl group, or form, together with the nitrogen atom, a group chosen from piperidyl and morpholinyl groups,
aryl and heteroaryl groups which may be substituted with one or more groups chosen independently from halogens, $C_1$–$C_4$ alkyl, trifluoromethyl, $C_1$–$C_4$ alkylthio, $C_1$–$C_4$ alkylsulphonyl, $C_1$–$C_4$ alkyloxy and nitro groups and groups —COOR, —CH$_2$COOR and —O—CH$_2$—COOR, R being a $C_1$–$C_4$ alkyl group,
and the oxo group is in position 2 or 3 on the piperazine; and the addition salts thereof with pharmaceutically acceptable acids.

As examples of aryl groups, mention may be made of phenyl, α-naphthyl, β-naphthyl and fluorenyl groups.

The $C_1$–$C_5$ alkyl groups may be linear or branched. Examples which may be mentioned are methyl, ethyl, propyl, isopropyl, butyl, isobutyl, tert-butyl and pentyl groups.

The alkynyl groups may be, for example, ethynyl, propargyl or butynyl groups.

The alkenyl groups may be, for example, vinyl and allyl groups.

The $C_1$–$C_4$ alkoxy groups may similarly be linear or branched. Examples which may be mentioned are methoxy, ethoxy, propoxy, isopropoxy, butoxy and isobutyoxy groups.

The halogens may be chosen from fluorine, chlorine, bromine and iodine.

As examples of protecting groups for the amidino group, mention may be made of ethoxycarbonyl, benzyloxycarbonyl, p-nitrobenzyloxycarbonyl and t-butoxycarbonyl groups.

The "addition salts with pharmaceutically acceptable acids" denote salts which give the biological properties of the free bases, without having any undesirable effect. These salts may be, in particular, those formed with mineral acids, such as hydrochloric acid, hydrobromic acid, sulphuric acid, nitric acid or phosphoric acid; acidic metal salts, such as disodium orthophosphate and monopotassium sulphate, and organic acids.

The compounds of formula I may be prepared by:

a) reacting an acid of formula

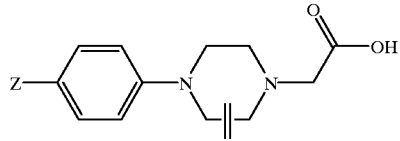

(II)

in which Z is a precursor group of a group

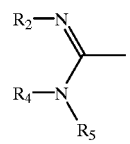

with an amine of formula

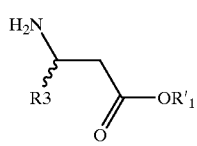
(III)

in which R'₁ is a $C_1$–$C_4$ alkyl or phenyl ($C_1$–$C_4$ alkyl) group, to give a compound of formula (IV)

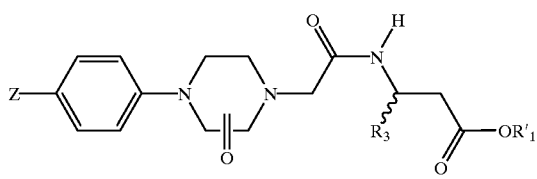

b) converting the group Z into a group

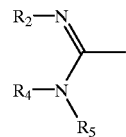

and c) optionally, converting the group R'₁ into a hydrogen atom.

The acids of formula II may be reacted with the amines of formula III in a polar solvent such as DMF, THF or ethyl acetate, in the presence of a coupling agent (DCC/HOBT, BOP, isobutyl chloroformate) at a temperature of from 15° C. to 50° C.

When Z is an N≡C— group, the group Z may be converted into an amidoxime by addition of hydroxylamine to the nitryl group in the presence of a suitable base ($K_2CO_3$, $Et_3N$, $NaOC_2H_5$) in an alcoholic solvent. Hydrogenolysis, in the presence of palladium-on-charcoal in a mixture of acetic anhydride and acetic acid, of the compounds obtained gives the compounds of formula I in which $R_2$ is hydrogen (with direct formation of a compound in which $R_1$=H when R'1 is a benzyl group).

When Z is an N≡C— group, the group Z can also be converted into an imidate by addition of ethanol in the presence of HCl in ethyl acetate. The imidate obtained is then converted into compounds of formula (I) in which $R_2$ is a hydrogen and —$NR_4R_5$ is either a piperidyl group or a morpholinyl group, by reaction with the corresponding amine in ethanol/ethyl acetate medium.

The compounds of formula II containing a 2-piperazinone group, when Z is a nitrile group, can be obtained according to the following scheme:

Scheme 1

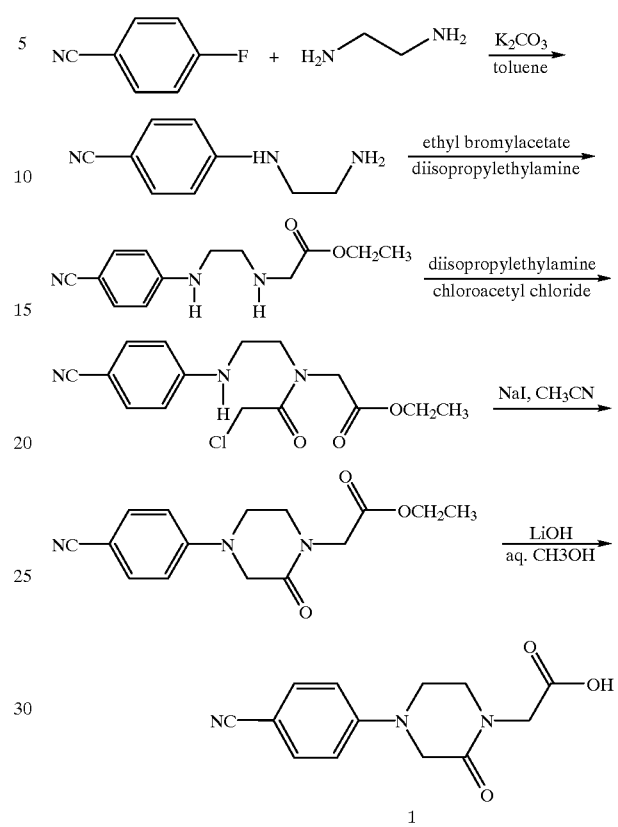

4-Fluorobenzonitrile is reacted with an excess of ethylenediamine in an aprotic solvent to give 4-(2-aminoethyl) benzonitrile, which is then mono-alkylated with ethyl bromoacetate in a polar solvent such as ethanol or acetonitrile, in the presence of an inorganic base or a tertiary amine. An acylation with chloroacetyl chloride followed by a cyclization and a hydrolysis give the acid (1).

The compounds of formula II containing a 3-piperazinone group, when Z is a nitrile group, can be obtained according to the following scheme:

Scheme 2

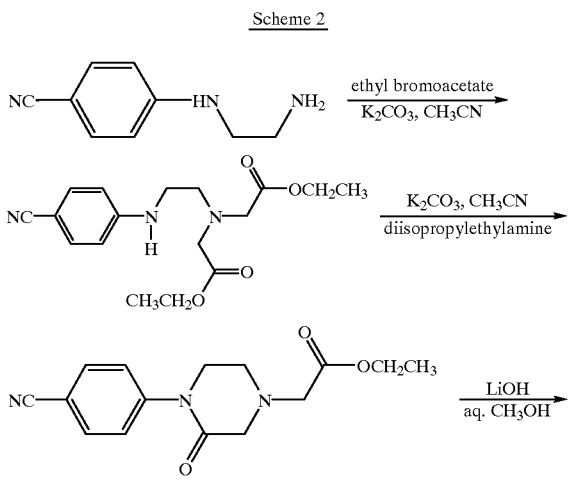

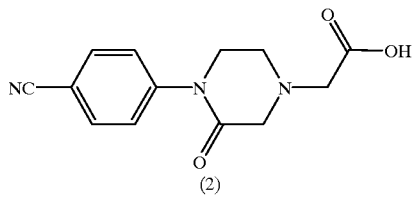

(2)

4-(2-Amioethyl)benzonitrile is dialkylated with ethyl bromoacetate; the cyclization is carried out in the presence of a tertiary amine, an inorganic base or a mixture thereof; after hydrolysis, the acid (2) is obtained.

The addition salts are obtained conventionally by reacting the compound of formula I with a pharmaceutically acceptable acid in a suitable solvent. Conversely, the bases may be obtained from the addition salts by treatment with a strong base.

The examples which follow illustrate the preparation of the compounds of formula I.

A—Preparation of the Compounds of Formula II

1. Synthesis of 2-[4-(4-cyanophenyl)-2-oxopiperazino] acetic acid (1)

a) 4-(2-aminoethylamino)benzonitrile

A suspension of 4-fluorobenzonitrile (167 g, 1.38 mol), ethylenediamine (330 g, 5.5 mol) and potassium carbonate (300 g, 2.17 mol) in 2 l of toluene is refluxed for 6 hours. After cooling to room temperature, the mixture is filtered and rinsed with toluene, and the filtrate is evaporated to give a yellow oil which is crystallized from toluene. The product is filtered off, rinsed with toluene and dried under vacuum at 50° C. to give 200 g of a slightly yellow solid.

Yield=90%

Melting point=85° C.

$^1$H-NMR (400 MHz, CDCl$_3$): δ1.2 (bs, 2H), 2.9 (t, 2H), 3.12 (q, 2H), 4.7 (bs, 1H), 6.5 (d, 2H), 7.3 (d, 2H).

b) Ethyl 2-{2-(chloroacetyl)-2-(4-cyanoanilino)-ethylamino} acetate

Ethyl bromoacetate (84 g, 0.5 mol) is added to a suspension of 4-(2-aminoethylamino)benzonitrile (80.5 g, 0.5 mol) and diisopropylethylamine (65 g, 0.5 mol) in 800 ml of acetonitrile. Stirring is then continued for 18 hours at room temperature. Most of the acetonitrile is evaporated off and the residue is taken up in dichloromethane. This mixture is washed with water and dried over sodium sulphate; the crude product is passed through a short column of silica [eluent: dichloromethane and then 20/1 dichloromethane/methanol] to give an oil.

The product obtained above is dissolved in 1 l of tetrahydrofuran; diisopropylethylamine (51 g, 0.4 mol) is added and chloroacetyl chloride (45 g, 0.4 mol) is then added slowly at ~5° C. After stirring for 18 hours at room temperature, 1 l of ethyl acetate is added and the mixture is washed with water 3 times, dried over sodium sulphate and then evaporated; a solid is obtained, which is stirred with a dichloromethane/ether mixture (1/3). The suspension is filtered and rinsed with dichloromethane/ether (1/3) and dried under vacuum to give 100 g of a crystalline beige-coloured solid.

Yield=62%

$^1$H-NMR (400 MHz, CDCl$_3$): δ1.2 (q, 6H), 3.3 (m, 4H), 3.65 (m, 4H), 3.8 (s, 2H), 3.9 (d, 4H), 4.1 (s, 4H), 4.15 (q, 4H), 4.9 (t, 1H), 5.3 (t, 1H), 6.5 (dd, 4H), 7.3 (dd, 4H).

c) Ethyl 2-[4-(4-cyanophenyl)-2-oxopiperazino]acetate

A suspension of ethyl 2-{2-(chloroacetyl)-2-(4-cyanoanilino)ethylamino} acetate (152 g, 0.47 mol), diisopropylethylamine (73 g, 0.57 mol) and sodium iodide (85 g, 0.57 mol) in 1.2 l of acetonitrile is refluxed for 2 hours. The solvent is evaporated off and the residue is taken up in dichloromethane, washed with water, dried over sodium sulphate and then evaporated to give a brown oil, which is crystallized from a cyclohexane/ethyl acetate mixture to give 125 g of a brownish crystalline solid.

Yield=93%

Melting point=108° C.

$^1$H-NMR (400 MHz, CDCl$_3$): δ1.3 (t, 3H), 3.65 (m, 4H), 4.05 (s, 2H), 4.2 (m, 4H), 6.8 (d, 2H), 7.5 (d, 2H).

d) 2-[4-(4-cyanophenyl)-2-oxopiperazino]acetic acid

Ethyl 2-[4-(4-cyanophenyl)-2-oxopiperazino]-acetate (20.7 g, 72 mmol) is dissolved in 80 ml of methanol, 80 ml of tetrahydrofuran and 100 ml of water, and lithium hydroxide monohydrate (4 g, 98 mmol) is then added. Stirring is continued for 20 minutes and the organic solvent is then removed under vacuum. About 100 ml of water are added to the suspension obtained and this mixture is acidified. The product is filtered off, rinsed with water and dried under vacuum at 50° C. to give 18.5 g of a beige-coloured powder.

Yield=100%

Melting point=215° C. (d).

$^1$H-NMR (200 MHz, DMSO-d$_6$): δ3.5 (t, 2H), 3.65 (t, 2H), 4.0 (s, 2H), 4.1 (s, 2H), 7.0 (d, 2H), 7.6 (d, 2H).

2. Synthesis of 2-[4-(4-cyanophenyl)-3-oxopiperazino] Acetic Acid (2)

a) Ethyl 2-[2-(4-cyanoanilino)ethyl(2-ethoxy-2-oxo-ethyl)amino]acetate

A suspension of 4-(2-aminoethylamino)-benzonitrile (1a) (32 g, 0.2 mol), potassium carbonate (55 g, 0.4 mol) and ethyl bromoacetate (67 g, 0.4 mol) in 400 ml of acetonitrile is refluxed for 18 hours. The crude product is filtered off and passed through a short column of silica (eluent: dichloromethane) to give 58 g of a brown oil.

Yield=87%.

$^1$H-NMR (200 MHz, CDCl$_3$) : δ1.3 (t, 3H) , 3.05 (t, 2H), 3.4 (s, 2H), 3.55 (s, 2H), 3.8 (t, 2H), 4.2 (q, 2H), 7.45 (d, 2H), 7.6 (d, 2H).

MS-Cl m/z: 287 (M+H)$^+$ b) 2-[4-(4-cyanophenyl)-3-oxopiperazino]acetic acid

A suspension of Ethyl 2-[2-(4-cyanoanilino)-ethyl (2-ethoxy-2-oxoethyl)amino]acetate (58 g, 0.174 mol), diisopropylethylamine (4 g, 0.03 mol) and potassium carbonate (24 g, 0.174 mol) in 400 ml of acetonitrile is refluxed for 2 days. The mixture is filtered and rinsed with dichloromethane. The filtrate is evaporated to give a brown solid, which is dissolved in 150 ml of methanol and 50 ml of water, and lithium hydroxide monohydrate (8.4 g, 0.2 mol) is then added. After stirring for 30 minutes at room temperature, half of the methanol is removed under vacuum to give a suspension. About 100 ml of water are added and this mixture is acidified at 5° C. The product is filtered off, rinsed with water and dried under vacuum at 50° C. to give 27.2 g of a beige-coloured powder.

Yield=55%

Melting point=120° C.

$^1$H-NMR (200 MHz, DMSO-d$_6$): δ2.95 (t, 2H), 3.3 (s, 2H), 3.4 (s, 2H), 3.7 (t, 2H), 7.65 (d, 2H), 7.85 (d, 2H).

B—Preparation of the Intermediate Products of Formula IV

1—Synthesis of ethyl 3-{[2-(4-(4-cyanophenyl)-2-oxopiperazino)acetyl]amino}propanoate (intermediate B1)

Isobutyl chloroformate (1.39 g, 10 mmol) is added to a suspension of 2-[4-(4-cyanophenyl)-2-oxopiperazino]acetic acid (2.59 g, 10 mmol) and N-methylmorpholine (2.1 g, 20.8 mmol) in 30 ml of tetrahydrofuran, at 5~10° C., after which the mixture is stirred at room temperature for 10 minutes; ethyl 3-aminopropanoate hydrochloride (1.55 g, 10 mmol) is then added. Stirring is continued for 1 hour; the solvent is evaporated off and the residue is purified by flash chromatography (15/1 dichloromethane/methanol) to give 2 g of a white solid.

Yield=56%

$^1$H-NMR (200 MHz, CDCl$_3$): δ1.25 (t, 3H), 2.5 (t, 2H), 3.5 (dd, 2H), 3.65 (m, 4H), 4.05 (s, 2H), 4.08(s, 2H), 4.1 (q, 2H), 6.75 (bs, 1H), 6.8 (d, 2H), 7.55 (d, 2H).

The method described in 1 was used to prepare the following intermediate products:

2—Benzyl 3-{[2-(4-(4-cyanophenyl)-2-oxopiperazino)-acetyl]amino}propanoate (intermediate B2)

Starting material: benzyl 3-aminopropanoate tosylate.

Yield=71%

$^1$H-NMR (200 MHz, CDCl$_3$): δ2.55 (t, 2H), 3.5 (q, 2H), 3.6 (s, 4H), 4.0 (s, 2H), 4.05 (s, 2H), 5.1 (s, 2H), 6.8 (m, 3H), 7.3 (m, 5H), 7.5 (d, 2H).

3—Ethyl 3-(1,3-benzodioxol-5-yl)-3-{[2-(4-(4-cyanophenyl)-2-oxopiperazino)acetyl]amino}propanoate (intermediate B3)

Starting material: ethyl 3-amino-3-(1,3-benzodioxol-5-yl) propanoate hydrchloride Yield=59%

$^1$H-NMR (400 MHz, CDCl$_3$) : δ1.15 (t, 3H), 2.8 (m, 2H), 3.65 (m, 4H), 4.1 (m, 6H), 5.3 (q, 1H), 5.9 (d, 2H), 6.85 (m, 5H), 6.9 (d, 1H), 7.5 (d, 2H).

4—Benzyl 3-(1,3-benzodioxol-5-yl)-3-{[2-(4-(4-cyanophenyl)-2-oxopiperazino)acetyl]amino}propanoate (intermediate B4)

Starting material: Benzyl 3-amino-3-(1,3-benzodioxol-5-yl) propanoate tosylate.

Yield=49%.

$^1$H-NMR (400 MHz, CDCl$_3$): δ2.8 (m, 2H), 3.55 (s, 4H), 4.0 (s, 2H), 4.1 (q, 2H), 5.0 (d, 2H), 5.3 (q, 1H), 5.9 (d, 2H), 6.7 (m, 6H), 7.25 (m, 6H), 7.5 (d, 2H).

5—Ethyl 3-{[2-(4-(4-cyanophenyl)-2-oxopiperazino)-acetyl]amino}-3-(pyridyl)propanoate (intermediate B5)

Starting material: ethyl 3-amino-3-(pyridyl)propanoate dihydrochloride.

Yield=54%

$^1$H-NMR (400 MHz, CDCl$_3$): δ1.05 (t, 3H), 2.85 (m, 2H), 3.65 (m, 4H), 4.1 (m, 6H), 5.4 (q, 1H), 6.75 (d, 2H), 7.25 (q, 1H), 7.5 (d, 2H), 7.65 (d, 1H), 7.75 (bs, 1H), 8.45 (d, 1H), 8.55 (s, 1H)

6—Benzyl 3-{[2-(4- (4-cyanophenyl) -2-oxopiperzino)-acetyl]amino}-3-(pyridyl)propanoate (intermediate B6)

Starting material: Benzyl 3-amino-3-(pyridyl)propanoate ditosylate.

Yield=48%/

$^1$H-NMR (400 MHz, CDCl$_3$): δ2.95 (dd, 2H), 3.6 (s, 4H) 4.0 (s, 2H), 4.1 (q, 2H), 5.0 (s, 2H), 5.45 (q, 1H), 6.75 (d, 2H), 7.25 (m, 6H), 7.5 (d, 2H), 7.65 (d, 1H), 7.75 (d, 1H), 8.5 (d, 1H) 8.6 (s, 1H).

7—Ethyl 3-{[2-(4-(4-cyanophenyl)-2-oxopiperazino)-acetyl]amino}-5-phenylpentanoate (intermediate B7)

Starting material Ethyl 3-amino-5-phenylpentanoate hydrochloride.

Yield=63%

$^1$H-NMR (400 MHz, DMSO-d$_6$): δ1.2 (t, 3H), 1.8 (m, 2H), 2.5 (dq 2H), 2.6 (t, 2H), 3.6 (dd, 4H), 4.1 (m, 6H), 4.2 (m, 1H), 6.65 (d, 1H), 6.75 (d, 2H), 7.1 (m, 3H), 7.2 (m, 3H), 7.5 (d, 2H).

8—Ethyl 3-{[2-(4-(4-cyanophenyl)-2-oxopiperazino) acetyl]amino}-3-cyclohexylpropanoate (intermediate B8)

Starting material: ethyl 3-amino-3-cyclohexylpropanoate hydrochloride

Yield=59%

$^1$H-NMR (400 MHz, DMSO-d$_6$): δ0.9 (m, 2H), 1.1 (m, 3H), 1.15 (t, 3H), 1.35, (m, 1H), 1.6 (m, 5H), 2.3 (dd, 1H), 2.5 (dd, 1H), 3.5 (m, 2H), 3.6 (m, 2H), 4.0 (m, 7H), 6.95 (d, 2H), 7.6 (d, 2H), 7.8 (d, 1H).

9—Ethyl 3-{[2-(4-(4-cyanophenyl)-2-oxopiperzino)-acetyl] amino}-5-methylhexanoate (intermediate B9)

Starting material: ethyl 3-amino-5-methylhexanoate hydrochloride

The crude product was used directly for Example 9.

10—Ethyl 3-{[2-(4-(4-cyanophenyl)-2-oxopiperazino)-acetyl]amino}-4,4-dimethylpentanoate (intermediate B10)

Starting material: ethyl 3-amino-4,4-dimethylpentanoate hydrochloride.

This product was used directly for Example 10.

11—Ethyl 3-{[2-(4-(4-cyanophenyl)-2-oxopiperazino)-acetyl]amino}-4-methylpentanoate (intermediate B11)

Starting material: ethyl 3-amino-4-methylpentanoate hydrochloride.

This product was used directly for Example 11.

12—Ethyl 3-{[2-(4-(4-cyanophenyl)-3-oxopiperazino) acetyl]amino}propanoate (intermediate B12)

Isobutyl chloroformate (1.39 g, 10 mmol) is added to a suspension of 2-[4-(4-cyanophenyl)-3-oxopiperazino]acetic acid (Example 2b) (2.59 g, 10 mmol) and N-methylmorpholine (2.1 g, 20 mmol) in 30 ml of tetrahydrofuran, after which the mixture is heated in a 40° C. bath for 5 minutes; next, ethyl 3-aminopropanoate hydrochloride (1.55 g, 10 mmol) is added. Stirring is continued at room temperature for 18 hours; the solvent is evaporated off and the residue is purified by flash chromatography (15/1 dichloromethane/methanol) to give 1.7 g of a white solid.

Yield=48%.

$^1$H-NMR (200 MHz, CDCl$_3$): δ1.25 (t, 3H), 2.6 (t, 2H), 2.95 (t, 2H), 3.15 (s, 1H), 3.4 (s, 2H), 3.55 (dd, 2H), 3.8 (dd, 2H), 4.1 (q, 2H), 7.45 (bs, 1H), 7.5 (d, 2H), 7.7 (d, 2H).

The method described in 12 was used to prepare the following intermediate products:

13—Benzyl 3{[2-(4-(4-cyanophenyl)-3-oxopiperazino)-acetyl]amino}propanoate (intermediate B13)

Starting material: benzyl 3-aminopropanoate tosylate

Yield: 69%

$^1$H-NMR (200 MHz, CDCl$_3$): δ2.6 (t, 2H), 2.8 (t, 2H), 3.1 (s, 2H), 3.4 (s, 2H), 3.55 (q, 2H), 3.65 (dd, 2H), 5.1 (s, 2H), 7.3 (s, 5H), 7.4 (bs, 1H), 7.45 (d, 2H), 7.6 (d, 2H).

14—Ethyl 3{[2-(4-(4-cyanophenyl)-3-oxopiperazino)-acetyl]amino}-3-(1,3-benzodioxol-5-yl)propanoate (intermediate B14)

Starting material: ethyl 3-amino-3-(1,3-benzodioxol-5-yl) propanoate hydrochloride.

Yield=48%.

15—Benzyl 3-{[2-(4-(4-cyanophenyl)-3-oxopiperazino) acetyl]amino}-3-(1,3-benzodioxol-5-yl)-propanoate (intermediate B15)

Starting material: benzyl 3-amino-3-(1,3-benzodioxol-5-yl) propanoate tosylate.

Yield=48%.

EXAMPLE 1

Ethyl 3-{[12-(4-{4-[amino(hydroxyimino)methyl] phenyl}-2-oxopiperazino)acetyl]amino}propanoate (CRL 42656)

A mixture of intermediate B1, ethyl 3-{[2-(4-(4-cyanophenyl)-2-oxopiperzino)acetyl]amino}-propanoate (6.2 g, 17.3 mmol), triethylamine (3.8 g, 37.6 mmol) and hydroxylamine hydrochloride (2.5 g, 6 mmol) in 150 ml of ethanol is refluxed for 3 hours. After cooling, the mixture is filtered, rinsed with ethanol and dried under vaccum to give 5.2 g of white crystals.

Yield=77%.

$^1$H-NMR (200 MHz, CD$_3$OD): δ1.25 (t, 3H) 2.55 (t, 2H), 3.45 (t, 2H), 3.58 (dd, 2H), 3.72 (dd, 2H), 4.0 (s, 2H), 4.1 (m, 4H), 7.0 (d, 2H), 7.6 (d, 2H).

MS-Cl m/z: 392 (M+H)$^+$.

The method described in Example 1 was used to prepare the following products:

EXAMPLE 2

Benzyl 3-{[2-(4-{4-[amino(hydroxyimino)methyl] phenyl}-2-oxopiperazino)acetyl]amino}propanoate Starting material: intermediate B2.

Yield=71%.

$^1$H-NMR (200 MHz, DMSO-d$_6$): δ2.55 (t, 2H), 3.4 (m, 6H), 3.85 (s, 2H), 4.0 (s, 2H), 5.1 (s, 2H), 5.6 (s, 2H), 6.9 (d, 2H), 7.34 (m, 4H), 7.55 (d, 2H), 8.05 (t, 1H), 9.35 (s, 1H).

EXAMPLE 3

Ethyl 3-{[2-(4-{4-[amino(hydroxyimino)methyl] phenyl}-2-oxopiperazino)acetyl]amino}-3-(1,3-benzodioxol-5-yl)propanoate (CRL 42789)

Starting material: intermediate B3.

Yield=77%.

$^1$H-NMR (400 MHz, DMSO-d6): δ1.1 (t, 3H), 2.75 (dd, 2H), 3.4 (bs, 2H), 3.5 (bs, 2H), 3.9 (s, 2H), 4.0 (s, 4H), 5.15 (q, 1H), 5.65 (s, 2H), 6.0 (s, 2H), 6.85 (m, 5H), 7.55 (d, 2H), 8.4 (d, 1H), 9.4 (s, 1H)

MS-ES m/z: 534 (M+Na)$^+$.

EXAMPLE 4

Benzyl 3-{[2-(4-{4-[amino(hydroxyimino)methyl] phenyl}-2-oxopiperazino) acetyl]amino}-3-(1,3-benzodioxol-5-yl) propanoate Starting material: intermediate B4.

Yield=73%.

$^1$H-NMR (400 MHz, DMSO-d$_6$): δ2.8 (dd, 2H), 3.45 (m, 2H), 3.5 (m, 2H), 3.8 (s, 2H), 4.0 (s, 2H), 5.0 (s, 2H), 5.1 (q, 1H), 5.6 (s, 2H), 6.0 (s, 2H), 6.8 (dd, 2H), 6.9 (m, 3H), 7.3 (m, 5H), 7.55 (d, 2H), 8.5 (d, 1H), 9.4 (s, 1H).

EXAMPLE 5

Ethyl 3-{[2-(4-{4-[amino(hydroxyimino)methyl] phenyl}-2-oxopiperazino)acetyl]amino}-3-(pyridyl) propanoate (CRL 42770)

Starting material: intermediate B5.

Yield=72%.

$^1$H-NMR (400 MHz, DMSO-d$_6$): δ1.15 (t, 3H), 3.0 (d, 2H), 3.45 (bs, 2H), 3.65 (bs, 2H), 4.0 (s, 2H), 4.05 (q, 2H), 4.1 (s, 2H), 5.4 (q, 1H), 7.0 (d, 2H), 7.7 (d, 2H), 8.1 (dd, 1H), 8.6 (bs, 1H), 8.65 (d, 1H), 8.8 (d, 1H), 8.95 (s, 1H), 9.15 (bs, 1H), 9.25 (d, 1H).

MS-ES m/z: 469 (M+H)$^+$.

EXAMPLE 6

Benzyl 3-{[2-(4-{4-[amino(hydroxyimino)methyl] phenyl}-2-oxopiperazino)acetyl]amino}-3-(pyridyl) propanoate Starting material: intermediate B6.

Yield=57%.

$^1$H-NMR (400 MHz, DMSO-d$_6$): δ2.9 (d, 2H), 3.5 (m, 4H) 3.85 (s, 2H), 4.0 (s, 2H), 5.0 (s, 2H), 5.25 (q, 1H), 5.6 (bs, 2H), 6.85 (d, 2H), 7.3 (m, 6H), 7.5 (d, 2H), 7.7 (d, 1H), 8.4 (d, 1H), 8.5 (s, 1H), 8.6 (d, 1H), 9.3 (s, 1H).

EXAMPLE 7

Ethyl 3-{[2-(4-{4-[amino(hydroxyimino)methyl] phenyl}-2-oxopiperazino)acetyl]amino}-5-phenylpentanoate (CRL 42903)

Starting material: intermediate B7.

Yield=73%.

$^1$H-NMR (400 MHz, DMSO-d$_6$): δ1.2 (t, 3H), 1.75 (m, 2H), 2.45~2.7 (m, 4H), 3.5 (dd, 4H), 3.85 (s, 2H), 4.1 (m, 5H), 5.7 (s, 2H), 6.9 (d, 2H), 7.2 (m, 3H), 7.25 (t, 2H), 7.6 (d, 2H), 7.95 (d, 1H), 9.2 (s, 1H).

MS-ES m/z: 518 (M+Na)$^+$

EXAMPLE 8

Ethyl 3-{[2-(4-{4-[amino(hydroximino)methyl] phenyl}-2-oxopiperazino)acetyl]amino}-3-cyclohexylpropanoate (CRL 42933)

Starting material: intermediate B8.

Yield=72%.

$^1$H-NMR (400 MHz, DMSO-d$_6$): δ0.9 (m, 2H), 1.1 (m, 3H), 1.15 (t, 3H), 1.35 (m, 1H), 1.6 (m, 5H), 2.3 (dd, 1H), 2.5 (dd, 1H), 3.5 (m, 2H), 3.6 (m, 2H), 4.0 (m, 7H), 6.95 (d, 2H), 7.6 (d, 2H), 7.8 (d, 1H), 9.4 (s, 1H).

MS-ES m/z: 496 (M+Na)$^+$

EXAMPLE 9

Ethyl 3-{[2-(4-{4-[amino(hydroxyimino)methyl] phenyl}-2-oxopiperazino)acetyl]amino}-5-methylhexanoate (CRL 42935)

Starting material: intermediate B9.

Yield=40% (for the two steps).

$^1$H-NMR (400 MHz, DMSO-d$_6$): δ0.9 (t, 6H), 1.17 (t, 3H), 1.20 (m, 1H), 1.4 (m, 1H), 1.6 (m, 1H), 2.4 (d, 2H), 3.4 (m, 2H), 3.5 (m, 2H), 3.8 (s, 2H), 4.0 (d, 2H), 4.1 35 .(q, 2H), 4.18 (m, 1H), 5.65 (s, 2H), 6.92 (d, 2H), 7.5 (d, 2H), 7.8 (d, 1H), 9.35 (s, 1H).

MS-ES m/z: 470 (M+Na)$^+$.

EXAMPLE 10

Ethyl 3-{[2-(4-{4-[amino(hydroxyimino)methyl] phenyl}-2-oxopiperazino)acetyl]amino}-4,4-dimethylpentanoate (CRL 42963)

Starting material: intermediate B10.

Yield=39% (for the two steps).

$^1$H-NMR (400 MHz, DMSO-d$_6$): δ0.85 (s, 9H), 1.20 (t, 3H), 2.25 (dd, 1H), 2.6 (dd, 1H), 3.45 (m, 2H), 3.5 (m, 2H), 3.85 (s, 2H), 4.05 {m, 5H), 5.7 (s, 2H), 6.95 (d, 2H), 10 7.6 (d, 2H), 7.85 (d, 1H), 9.4 (s, 1H).

MS-ES m/z: 470 (M+Na)$^+$.

EXAMPLE 11

Ethyl 3-{[2-(4-{4-[amino(hydroxyimino)methyl] phenyl}-2-oxopiperazino)acetyl]amino}-4-methylpentanoate (CRL 42965)

Starting material: intermediate B11.

Yield=36% (for the two steps).

$^1$H-NMR (400 MHz, DMSO-d$_6$): δ0.85 (d, 6H), 1.2 (t, 3H), 1.75 (m, 1H), 2.4 (dd, 1H), 2.55 (dd, 1H), 3.45 (m, 2H), 3.55 (m, 2H), 3.8 (s, 2H), 4.1 (m, 5H), 5.7 (s, 2H), 6.95 (d, 2H), 7.6 (d, 2H), 7.85 (d, 1H), 9.45 (s, 1H).

MS-ES m/z: 456 (M+Na)$^+$

EXAMPLE 12

Ethyl 3-{[2-(4-{4-[amino(hydroxyimino)methyl]phenyl}-3-oxopiperazino)acetyl]amino}propanoate (CRL 42655)

A solution of intermediate B12, ethyl 3-{2-[4-(4-cyanophenyl)-3-oxopiperazino)acetyl]amino}-propanoate (4.96 g, 13.9 mmol), triethylamine (2.9 g, 28.7 mmol) and hydroxylamine hydrochloride (2 g, 28.8 mmol) in 200 ml of ethanol is refluxed for 4 hours and the solvent is then removed under vacuum. About 30 ml of water are added and the solution is saturated with sodium chloride. The resulting mixture is filtered, rinsed with cold water and dried under vacuum to give 3 g of a beige-coloured solid.

Yield=55%.

$^1$H-NMR (200 MHz, DMSO-$d_6$): δ1.10 (t, 3H), 2.75 (t, 2H), 3.0 (s, 2H), 3.2 (s, 2H), 3.25 (m, 4H), 3.65 (t, 2H), 4.0 (q, 2H), 5.75 (bs, 2H), 7.25 (d, 2H), 7.6 (d, 2H), 7.95 (bs, 1H), 9.5 (s, 1H).

MS-ES m/z: 392 (M+H)$^+$

The method described in Example 12 was used to prepare the following products:

EXAMPLE 13

Benzyl 3-{[2-(4-{4-[amino(hydroxyimino)methyl]phenyl}-3-oxopiperazino)acetyl]amino}propanoate
Starting material: intermediate B13.
Yield=86%.

EXAMPLE 14

Ethyl 3-{[2-(4-{4-[amino(hydroxyimino)methyl]phenyl}-3-oxopiperazino)acetyl]amino}-3-(1,3-benzodioxol-5-yl)propanoate (CRL 42838)

$^1$H-NMR (400 MHz, DMSO-$d_6$): δ1.1 (t, 3H), 2.8 (m, 4H), 3.1 (q, 2H), 3.35 (s, 2H), 3.75 (t, 2H), 4.0 (q, 2H), 5.2 (q, 1H), 5.8 (s, 2H), 6.0 (s, 2H), 6.8 (dd, 2H), 7.0 (s, 1H), 7.3 (d, 2H), 7.55 (d, 2H), 8.4 (d, 1H), 9.65 (s, 1H).

MS-ES m/z: 534 (M+Na)$^+$

EXAMPLE 15

Benzyl 3-{[2-(4-{4-amino(hydroxyimino)phenyl}-3-oxo-piperazino) acetyl]amino}-3-(1,3-benzodioxol-5-yl)propanoate
Starting material: intermediate B15.
Yield=92%.

EXAMPLE 16

Ethyl 3-{[2-(4-{4-[amino(imino)methyl]phenyl}-2-oxopiperazino)acetyl]amino}proanoate acetate (CRL 42673)

Ethyl 3-{[2-(4-{4-[amino(hydroxyimino)-methyl]phenyl}-2-oxopiperazino)acetyl]amino}propanoate (Example 1) (2.88 g, 7.36 mmol) is dissolved in 100 ml of acetic acid, and acetic anhydride (1.5 g, 14.7 mmol) and 0.5 g of 10% palladium-on-charcoal are then added. The mixture is hydrogenated at room temperature under 50 psi for 3 hours. The resulting mixture is filtered and evaporated to dryness under vacuum to give a powder, ether is added and the suspension thus obtained is filtered to give 2.8 g of a slightly pink powder, which is dissolved in 100 ml of water, treated with charcoal and filtered, and the filtrate is freeze-dried to give 2.5 g of a beige-coloured solid.

Yield=78%.

$^1$H-NMR (400 MHz, DMSO-$d_6$): δ1.3 (t, 3H), 1.8 (s, 3H), 3.4 (dd, 2H), 3.6 (t, 2H), 3.8 (t, 2H), 4.0 (d, 4H), 4.05 (q, 2H), 7.2 (d, 2H), 7.85 (d, 2H), 8.25 (bs, 1H).

MS-ES m/z: 376 (M+H)$^+$.

The method described in Example 16 was used to prepare the following products (with conversion of the acetate into hydrochloride for the compounds of Examples 17, 19, 28 and 30).

EXAMPLE 17

3-{[2-(4-{4-[amino(imino)methyl]phenyl}-2-oxopiperazino)acetyl]amino}propanoic acid hydrochloride (CRL 42674)

Starting material: Example 2.
Yield=88%.

$^1$H-NMR (200 MHz, DMSO-$d_6$): δ2.35 (t, 2H), 3.25 (dd, 2H), 3.35~3.7 (m, 4H), 4.0 (d, 4H), 7.0 (d, 2H), 7.8 (d, 2H), 8.1 (bs, 1H), 8.85 (bd, 2H), 9.05 (bs, 2H).

MS-ES m/z: 348 (M+H)$^+$.

EXAMPLE 18

Ethyl 3-{[2-(4-{4-[amino(imino)methyl]phenyl}-2-oxopiperazino)acetyl]amino}-3-(1,3-benzodioxol-5-yl)propanoate acetate (CRL 42827)

Starting material: Example 3.
Yield=68%.

$^1$H-NMR (400 MHz, DMSO-$d_6$): δ1.1 (t, 3H), 1.7 (s, 3H), 2.75 (dd, 2H), 3.5 (t, 2H), 3.7 (t, 2H), 4.0 (m, 6H), 5.2 (q, 1H), 6.0 (s, 2H), 6.8 (dd, 1H), 6.85 (d, 1H), 5 6.9 (s, 1H), 7.0 (d, 2H), 7.75 (d, 2H) , 8.55 (d, 1H) MS-ES m/z: 496 (M+H)$^+$.

EXAMPLE 19

3-{[2-(4-{4-[amino(imino)methyl]phenyl}-2-oxopiperazino)acetyl]amino}-3-(1,3-benzodioxol-5-yl)propanoic acid hydrochloride (CRL 42788)

Starting material: Example 4.
Yield=47%.

$^1$H-NMR (400 MHz, DMSO-$d_6$): δ2.65 (t, 2H), 3.5 (bs, 2H), 3.7 (bs, 2H), 4.05 (d, 4H), 5.2 (q, 1H), 6.0 (s, 2H), 6.75 (d, 1H), 6.8 (d, 1H), 6.9 (s, 1H), 7.05 (d, 2H), 7.8 (d, 2H), 8.7 (d, 1H), 9.0 (bs, 2H), 9.1 (bs, 2H), 12.3 (bs, 1H).

MS-Cl m/z: 468 (M+H)$^+$.

EXAMPLE 20

Ethyl 3-{[2-(4-{4-[amino(imino)methyl]phenyl}-2-oxopiperazino)-acetyl]amino}-3-(pyridyl)propanoate acetate (CRL 42828)

Starting material: Example 5.
Yield=75%.

$^1$H-NMR (400 MHz, DMSO-$d_6$): δ1.1 (t, 3H), 1.75 (bs, 3H), 2.9 (d, 2H), 3.45 (bs, 2H), 3.7 (bs, 2H), 4.0 (m, 6H), 5.2 (q, 1H), 7.0 (d, 2H), 7.4 (t, 1H), 7.8 (bd, 3H), 8.45 (bs, 1H), 8.5 (bs, 1H), 8.8 (bd, 1H).

MS-ES m/z: 453 (M+H)$^+$.

EXAMPLE 21

3-{[2-(4-{4-[amino(imino)methyl]phenyl}-2-oxopiperazino)acetyl]amino}-3-(pyridyl)propanoic acid acetate (CRL 42799)

Starting material: Example 6.

Yield=67%.

$^1$H-NMR (400 MHz, DMSO-$d_6$): δ1.9 (s, 6H), 2.65 (bs, 2H), 3.5 (bs, 2H), 3.7 (bs, 2H), 3.9 (d, 1H), 4.05 (s, 2H), 4.2 (d, 1H), 5.2 (bs, 1H), 6.9 (d, 2H), 7.3 (dd, 1H), 7.7 (d, 2H), 7.75 (d, 1H), 8.4 (bs, 2H), 8.55 (s, 1H), 9.4 (bd, 1H), 11.1 (bs, 2H).

MS-Cl m/z: 425 (M+H)$^+$.

EXAMPLE 22

Ethyl 3-{[2-(4-{4-[amino(imino)methyl]phenyl}-2-oxopiperazino)acetyl]amino}-5-phenylpentanoate acetate (CRL 42904)

Starting material: Example 7.

Yield=70%.

$^1$H-NMR (400 MHz, DMSO-$d_6$): δ1.15 (t, 3H), 1.73 (s, 3H), 1.74 (m, 2H), 2.45 (m, 2H), 2.6 (m, 2H), 3.5 (m, 2H), 3.7 (m, 2H), 4.0 (m, 7H), 7.05 (d, 2H), 7.2 (m, 3H), 7.26 (t, 2H), 7.75 (d, 2H), 8.0 (d, 1H).

MS-ES m/z: 480 (M+H)$^+$

EXAMPLE 23

Ethyl 3-{[2-(4-{4-[amino(imino)methyl]phenyl}-2-oxopiperazino)acetyl]amino}-3-cyclohexylpropanoate acetate (CRL 42932)

Starting material: Example 8.

Yield=62%.

$^1$H-NMR (400 MHz, D$_2$O,: δ1.05 (m, 2H), 1,25 (m, 3H), 1.3 (t, 3H), 1.5 (m, 1H), 1.75 (m, 5H), 2.0 (s, 3H), 2.55 (dd, 1H), 2.8 (dd, 1H), 3.68 (m, 2H), 3.85 (m, 2H), 4.2 (m, 7H), 7.12 (d, 2H), 7.8 (d, 2H).

MS-ES m/z: 458 (M+H)$^+$.

EXAMPLE 24

Ethyl 3-{[2-(4-{4-[amino(imino)methyl]phenyl}-2-oxopiperazino)acetyl]amino}-5-methylhexanoate acetate (CRL 42934)

Starting material: Example 9.

Yield=74%.

$^1$H-NMR (400 MHz, D$_2$O): δ1.15 (t, 3H), 1.73 (s, 3H), 1.74 (m, 2H), 2.45 (m, 2H), 2.6 (m, 2H), 3.5 (m, 2H), 3.7 (m, 2H), 4.0 (m, 7H), 7.05 (d, 2H), 7.2 (m, 3H), 7.26 (t, 2H) 7.75 (d, 2H), 8.0 (d, 1H)

MS-ES m/z: 432 (M+H)$^+$.

5EXAMPLE 25

Ethyl 3-{[2-(4-{4-[amino(imino)methyl]phenyl}-2-oxopiperazino)acetyl]amino}-4,4-dimethylpentanoate acetate (CRL 42964)

Starting material: Example 10.

Yield=74%. $^1$H-NMR (400 MHz, D$_2$O): δ1.0 (s, 9H), 1.35 (t, 3H), 2.05 (s, 3H), 2.5 (dd, 1H), 2.85 (dd, 1H), 3.7 (m, 2H), 3.85 (m, 2H), 4.2 (m, 7H), 7.15 (d, 2H), 7.8 (d, 2H)

MS-ES m/z: 432 (M+H)$^+$.

EXAMPLE 26

Ethyl 3-{[2-(4-{4-[amino(imino)methyl]phenyl}-2-oxopiperazino)acetyl]amino}-4-methylpentanoate acetate (CRL 42966)

Starting material: Example 11.

Yield=100%.

$^1$H-NMR (400 MHz, D$_2$O): δ1.0 (t, 6H), 1.35 (t, 3H), 1.9 (m, 1H), 2.0 (s, 3H), 2.55 (dd, 1H), 2.8 (dd, 1H), 3.7 (m, 2H), 3.8 (m, 1H), 4.2 (m, 7H), 7.1 (d, 2H), 7.8 (d, 2H).

MS-ES m/z: 418 (M+H)$^+$.

EXAMPLE 27

Ethyl 3-{[2-(4-{4-[amino(imino)methyl]phenyl}-3-oxopiperazino)acetyl]amino}propanoate acetate (CRL 42672)

Starting material: Example 12.

Yield=53%.

$^1$H-NMR (200 MHz, DMSO-$d_6$): δ1.2 (t, 3H), 1.75 (s, 3H), 35 2.5 (s, 2H), 2; 85 (s, 2H), 3.3 (s, 4H), 3.8 (s, 2H), 4.05 (d, 2H), 7.6 (d, 2H), 7.8 (d, 2H), 8.1 (s, 1H).

EXAMPLE 28

3-{[2-(4-{4-[amino(imino)methyl]phenyl}-3-oxopiperazino)acetyl]amino}propanoic acid hydrochloride (CRL 42675)

Starting material: Example 13.

Yield=70%.

$^1$H-NMR (400 MHz, DMSO-$d_6$): (bs 2H), 2.5 (s, 2H), 2.8 (bs, 2H), 3.1 (s, 2H), 3.3 (m, 2H), 3.8 (bs, 2H), 7.55 (d, 2H), 7.65 (d, 2H), 8.2 (bs, 1H), 8.9 (bs, 1H).

MS-ES m/z: 370 (M+Na)$^+$.

EXAMPLE 29

Ethyl 3-{2-[4-(4-[amino(imino)methyl]phenyl}-3-oxopiperazino)acetyl]amino}-3-(1,3-benzodioxol-5-yl)propanoate acetate (CRL 42837)

Starting material: Example 14.

Yield=80%.

$^1$H-NMR (400 MHz, DMSO-$d_6$): δ1.1 (t, 3H), 1.75 (bs, 3H), 2.8 (m, 4H), 3.1 (q, 2H), 3.3 (s, 2H), 3.75 (bs, 2H), 4.0 (q, 2H), 5.2 (q, 1H), 6.0 (s, 2H), 6.75 (m, 2H), 6.9 (s, 1H), 7.55 (d, 2H), 7.8 (d, 2H), 8.45 (d, 1H).

MS-ES m/z: 496 (M+H)$^+$.

EXAMPLE 30

3-{[2-(4-{4-[amino(imino)methyl]phenyl}-3-oxopiperazino)acetyl]amino}-3-(1,3-benzodioxol-5-yl)propanoic acid hydrochloride (CRL 42839)

Starting material: Example 15.

Yield=76%.

$^1$H-NMR (400 MHz, DMSO-$d_6$): δ2.75 (m, 2H), 3.65 (bs, 2H), 4.1 (m, 6H), 5.2 (q, 1H), 5.95 (s, 2H), 6.8 (m, 2H), 7.0 (s, 1H), 7.6 (d, 2H), 7.9 (d, 2H), 9.25 (s, 3H), 9.45 (s, 2H) MS-ES m/z: 468 (M+H)$^+$.

EXAMPLE 31

Ethyl 3-({2-[4-(4-{amino[(ethoxycarbonyl)imino]-methyl}phenyl)-2-oxopiperazino]acetyl}amino)-3-(1,3-benzodioxol-5-yl)propanoate (CRL 42960)

The product of Example 18 is converted into the hydrochloride by addition of 2N hydrochloric acid HCl solution followed by filtration.

Triethylamine (1.1 g, 11 mmol) and ethyl chloroformate (0.54 g, 5 mmol) are added successively, at 5° C., to a solution of the hydrochloride thus obtained (2.2 g, 4.1 mmol) in 50 ml of DMF. Stirring is continued at room temperature for 18 hours. Water and ethyl acetate are added and the organic phase is washed with water and dried over sodium sulphate. 1.3 g of a yellowish solid are obtained after chromatography on silica (10/1 ethyl acetate/methanol).

Yield=55%.

$^1$H-NMR (400 MHz, CDCl$_3$) δ1.3 (t, 3H), 1.5 (t, 3H), 2.9 (dq, 2H), 3.75 (bs, 4H), 4.2 (m, 6H), 4.4 (q, 2H), 5.45 (m, 1H), 6.05 (d, 2H), 6.9 (m, 5H), 7.55 (d, 1H), 8.0 (d, 2H), 9.75 (bs, 1H).

MS-ES m/z: 590 (M+Na)$^+$.

EXAMPLE 32

Ethyl 3-{[2-(4-{4-[imino(piperidino)methyl] phenyl}-2-oxopiperazino)acetyl]amino}-5-phenylpentanoate (CRL 43101)

60 ml of a 4N hydrochloric ethyl acetate solution are added, at 5° C., to a mixture of ethyl 3-{[2-(4-(4-cyanophenyl)-2-oxopiperazino)acetyl]amino}-5-phenylpentanoate (intermediate B7) (3.3 g, 7.1 mmol) in 5 ml of ethanol. Stirring is continued at room temperature for 40 hours. The mixture is evaporated to dryness to give a yellowish solid.

Piperidine (2.6 g, 30.6 mmol) is added to a suspension of the imidate obtained above (2.1 g, 3.8 mmol) in 10 ml of ethanol and 50 ml of ethyl acetate. After stirring for 24 hours at room temperature, the mixture is filtered. The crude product is recrystallized from a mixture of ethyl acetate and ethanol to give 0.7 g of a beige-coloured solid.

Yield=65%.

$^1$H-NMR (400 MHz, DMSO-d$_6$): δ1.15 (t, 3H), 1.7 (m, 8H), 2.5 (m, 3H), 2.6 (m, 1H), 3.45 (m, 1H), 3.50 (bs, 4H), 3.70 (bs, 4H), 4.05 (m, 6H), 7.1 (d, 2H), 7.2 (m, 3H), 7.25 (d, 2H), 7.45 (d, 2H), 8.15 (d, 1H), 9.2 (bs, 2H)

MS-ES m/z: 548 (M+H)$^+$.

The method described in Example 32 was used to prepare the following products:

EXAMPLE 33

Ethyl 3-{[2-{4-{4-[imino(morpholino)methyl] phenyl}-2-oxopiperazino)acetyl]amino)-5-phenylpentanoate (CRL 43102)

Starting material: intermediate B7 and morpholine.

Yield=56%.

$^1$H-NMR (400 MHz, DMSO-d$_6$): δ1.15 (t, 3H), 1.7 (m, 2H), 2.5 (m, 3H), 2.6 (m, 1H), 3.50 (bs, 4H), 3.70 (m, 8H), 4.05 (m, 7H), 7.1 (d, 2H), 7.2 (m, 3H), 7.25 (d, 2H), 7.50 (d, 2H), 8.15 (d, 1H), 9.4 (bs, 2H).

MS-ES m/z: 550 (M+H)$^+$.

EXAMPLE 34

Ethyl 3-(1,3-benzodioxol-5-yl)-3-{[2-(4-{4-[imino (piperidino)methyl]phenyl}-2-oxopiperazino)-acetyl]amino}propanoate hydrochloride (CRL 43103)

Starting material: intermediate B3 and piperidine.

Yield=61%.

$^1$H-NMR (400 MHz, DMSO-d$_6$): δ1.15 (t, 3H), 1.65 (bs, 6H), 2.75 (m, 2H), 3.45 (m, 4H), 3.55 (m, 2H), 3.65 (bs, 2H), 4.00 (m, 6H), 5.15 (q, 1H), 6.00 (s, 2H), 6.8 (d, 1H), 6.85 (d, 1H), 6.95 (s, 1H), 7.05 (d, 2H), 7.45 (d, 2H), 8.7 (d, 1H), 9.15 (bs, 2H).

MS-ES m/z: 564 (M+H)$^+$

EXAMPLE 35

Ethyl 3-(1,3-benzodioxol-5-yl)-3-{[2-(4-{4-[imino-(morpholino)methyl]phenyl}-2-oxopiperazino) acetyl]-amino}propanoate hydrochloride (CRL 43104)

Starting material: intermediate B3 and morpholine.

Yield=65%.

$^1$H-NMR (400 MHz, DMSO-d$_6$): δ1.15 (t, 3H), 2.75 (m, 2H), 3.45 (m, 4H), 3.65 (m, 4H), 3.8 (bs, 4H), 4.00 (m, 6H), 5.15 (q, 1H), 6.00 (s, 2H), 6.75 (d, 1H), 6.80 (d, 1H), 6.90 (s, 1H), 7.05 (d, 2H), 7.45 (d, 2H), 8.65 (d, 1H), 9.30 (bs, 1H), 9.35 (bs, 1H).

MS-ES m/z: 566 (M+H)$^+$

A study of the inhibitory activity of the compounds of formula I on platelet aggregation was carried out in vitro, i.e. by direct contact of solutions of variable concentrations of the compounds with platelets freshly separated from a sample of whole blood, taken under standardized conditions, from laboratory animals (guinea pigs) and from healthy human subjects who have not received any substances or drugs that might interfere with blood clotting. The anti-platelet-aggregating activity was also studied ex vivo/vitro, i.e. after administration of the substances claimed in guinea pigs to measure the intensity and duration of the anti-aggregating action induced by the fraction of the test product absorbed and circulating in the blood.

1. In vitro Pharmacological Studies 1.1. Studies on Guinea Pig Platelets

Blood is taken by intracardiac puncture from male Dunkin-Hartley guinea pigs (weighing about 330 g), at a rate of 4.5 ml per 0.5 ml of trisodium citrate (concentration of the aqueous solution: 1.55%) in order to prevent all trace of clotting. The platelet-rich plasma (PRP) is obtained by centrifuging the tubes of whole blood for 15 minutes at 150 g.

The PRPs are collected as. "pools". The platelets contained in these pools are counted using a Coulter ZM haematology automatic device: if necessary, a dilution is carried out in order for the platelet concentration in the plasma to be between 200,000 and 400,000 platelets/mm$^3$. Simultaneously, other samples of these pools serve to prepare the platelet-poor plasma (PPP) by centrifugation at 1,500 g for 15 minutes.

The kinetic study of the platelet aggregation is carried out by adding a collagen solution (1 μg/ml) to a volume of PRP, using a Chrono-log Corporation aggregometer (490-D$_1$ or 560 VS) which uses an optical detection of the appearance of the thrombus.

The determination of the 50% inhibitory concentration (IC$_{50}$) is carried out by adding a given volume of solvent (control reference) and increasing concentrations: 1.5×10$^{-8}$ M, 7×10$^{-8}$ M, 1.5×10$^{-7}$ M, 3×10$^{-7}$ M, 7×10$^{-7}$ M, 1.5×10$^{-6}$ M and 7×10$^{-5}$ M, of the compounds to samples of the pools of PRP. The measurements of the aggregation inhibition are carried out after 3 minutes of contact at 37° C. with agitation.

1.2 Study on Human Platelets

Venous blood is taken from a group of ten healthy human subjects of the same age, by puncture into a vein of the fold of the elbow and is collected in a glass tube containing aqueous 0.129 M sodium citrate solution (1 volume of citrate solution per 9 volumes of blood). Each tube is then centrifuged a first time at 20° C. and 100 g for 15 minutes in order to obtain the platelet-rich plasma (PRP); after removing this PRP, the tube is again centrifuged at 2,000 g for 15 minutes in order this time to remove the platelet-poor plasma (PPP).

For each identified sample of PRP, the platelets are counted using a Coulter ZM counter. Each sample is then used to study the variation in inhibition of the platelet aggregation triggered by the addition of a Chromo-par Reagent collagen glucose solution from Coultronics (used at a concentration of 5 μg/ml) as a function of the addition of increasing concentrations of each compound in a range covering the interval $10^{-8}$ M→$10^{-5}$ M, (example of concentrations: $10^{-8}$ M, $5\times10^{-7}$ M, $3\times10^{31\ 7}$ M, $10^{-7}$ M, $8\times10^{-6}$ M, $4\times10^{-6}$ M, $2\times10^{-6}$ M, $10^{-6}$ M, $5\times10^{-5}$ M, $10^{-5}$ M). Beforehand, for each compound, an aqueous $10^{-3}$ M solution is prepared. A control test intended to check the possible effect of the solvents (reference value) on the platelet aggregation is introduced into each measurement series, and is measured after 3 minutes of contact at 37° C. with agitation.

From the percentages of inhibition of the platelet aggregation measured for each concentration of each compound, the 50% inhibitory concentration ($IC_{50}$) is calculated.

2. ex vivo/vitro Pharmacological Study in Guinea Pigs

Evaluation of the anti-platelet-aggregating activity of the compounds is carried out in the same guinea pigs as those mentioned above (Dunkin-Hartley strain). The administration of each product in a range of doses from 150 mg/kg to 10 mg/kg and of each vehicle (5 ml/kg) is carried out via the gastric route (g.r.) 1h or 2h or 4h or 6h or 8h or 12h before blood is taken from the guinea pigs fasted the day before. The allocation of the treatments to the animals is random.

The blood is taken and then treated under the same conditions as those described above for the in vitro studies.

The results of the inhibition of the platelet aggregation obtained for each test concentration make it possible to calculate the $IC_{50}$ concentration of each test product and the kinetics of the inhibitory effect and its duration of action.

The results for the studies of the inhibition platelet aggregation induced by collagen are collated in the following table:

| Examples | Compound CRL | $IC_{50}$ (M) in vitro Guinea pig | Man | % of g.r. inhibition guinea pig ex vivo d = 150 mg/kg −1 h | −2 h |
|---|---|---|---|---|---|
| 1 | 42656 | >$10^{-3}$ | — | −72 | −73 |
| 16 | 42673 | $3.8 \times 10^{-6}$ | — | −75 | −73 |
| 17 | 42674 | $4.8 \times 10^{-6}$ | $5.2 \times 10^{-6}$ | −43 | −38 |
| 27 | 42672 | $3.8 \times 10^{-5}$ | — | −8 | −9 |
| 28 | 42675 | $1.6 \times 10^{-5}$ | $1.4 \times 10^{-6}$ | −28 | −23 |
| 5 | 42770 | $1.0 \times 10^{-4}$ | — | −72 | −75 |
| 19 | 42788 | $1.5 \times 10^{-7}$ | $3.4 \times 10^{-7}$ | −69 | −78 |
| 3 | 42789 | UD | UD | −72 | −69 |
| 21 | 42799 | $1.6 \times 10^{-7}$ | $8.6 \times 10^{-7}$ | −78 | −79 |
| 18 | 42827 | $2.0 \times 10^{-7}$ | $8.1 \times 10^{-5}$ | −70 | −69 |
| 20 | 42828 | $6.3 \times 10^{-7}$ | $2.8 \times 10^{-5}$ | −65 | −64 |
| 30 | 42839 | $1.5 \times 10^{-5}$ | $1.2 \times 10^{-6}$ | −14 | −17 |
| 22 | 42904 | $5.1 \times 10^{-7}$ | $7.1 \times 10^{-5}$ | — | — |
| 23 | 42932 | $4.6 \times 10^{-5}$ | — | — | — |
| 24 | 42934 | $4.6 \times 10^{-6}$ | — | — | — |
| 25 | 42964 | $4.4 \times 10^{-4}$ | — | — | — |
| 26 | 42966 | $4.5 \times 10^{-6}$ | — | — | — |
| 32 | 43101 | $2.4 \times 10^{-6}$ | — | — | — |
| 33 | 43102 | $6.5 \times 10^{-7}$ | — | — | — |
| 34 | 43103 | $9.9 \times 10^{-7}$ | — | — | — |
| 35 | 43104 | $4.7 \times 10^{-7}$ | — | — | — |

UD: undeterminable (insoluble product)
—: data not available.

For certain compounds, the power of the inhibitory activity on platelet aggregation is found at much lower doses. This is the case, for example, for CRL 42789, CRL 42788 and CRL 42903, for which the anti-aggregating action, obtained ex-vivo in guinea pigs treated with an oral dose (gastric route) of 10 mg/kg, when the administration is carried out 1h and 2h before the aggregation test, is 69% and 72% (CRL 42789), 57% and 24% (CRL 42788) or 72% (at 1h for CRL 42903), respectively.

A subject of the present invention is thus also pharmaceutical compositions comprising an effective amount of a compound of formula (I) or of a salt thereof with pharmaceutically acceptable acids.

A subject of the invention is, more particularly, compounds for inhibiting the aggregation of blood platelets, comprising an effective amount of one of these compounds.

A subject of the invention is also
- a process for inhibiting the binding of fibrinogen to blood platelets in a mammal, comprising the administration to this mammal of an effective amount of one of these compounds,
- a process for inhibiting the aggregation of blood platelets in a patient, comprising the administration of an effective amount of one of these compounds to this patient;
- a process for treating a thrombus in a patient, comprising the administration to this patient of an effective amount of one of these compounds,
- a process for preventing the risk of thrombosis in a patient, comprising the administration to this patient of an effective amount of one of these compounds.

The compounds of formula (I) can be used, in particular, in the following fields:

i) Acute prevention of the arterial risk of thrombosis in the course of heart surgery (coronary bypass) or interventional cardiology (transluminal percutaneous angioplasty, endartectomy, insertion of a stent): in these situations, the compounds are added to the recognized preventive treatment of the arterial risk of thrombosis; oral administration of acetylsalicylic acid starting before the intervention (150 to 500 mg/j orally) and then continues as follows; intravenous infusion of non-fractionated heparin starting during the intervention and then continuing for 48 to 96 hours. The administration of the compound of formula I can then be carried out either orally (0.5 to 1.5 mg/kg) at the same time as the administration of aspirin, or by intravenous infusion (0.25 to 1 mg/kg/24h) combined or not combined with a bolus. After the $_{48}$th hour, if the treatment was administered intravenously, it will be relayed by the oral administration (0.25 to 10 mg/kg in two dosage intakes with an interval of 12 hours) in order to facilitate the hospitalization care and then the ambulatory treatment.

(ii) Secondary prophylaxis of the arterial risk of thrombosis in patients liable to exhibit episodes of unstable angina or a myocardial infarction: in these situations, the large bioavailability of the compounds claimed, i.e. the possibility of rapidly obtaining circulating concentrations that are effective since they are capable of inhibiting the binding of fibrinogen to platelets, makes it possible to use the medicines claimed orally during the period in which the patients show this risk of arterial thrombosis. In these situations, these compounds may be administered advantageously at a rate of 1 to 3 oral doses per day, by virtue of their high bioavailability and their long duration of action, the dose being chosen in the range 0.5–10 mg/kg.

The pharmaceutical compositions which comprise one of the active principles described in the present patent application incorporate the active substance either in the form of base or in the form of a pharmaceutically acceptable salt, or alternatively in the form of a prodrug comprising one or more protective functions, these functions then being released in vivo after oral administration. These pharmaceutical compositions incorporate the manufacturing adjuvants or vehicles that are known to those skilled in the art. The latter are chosen from the range of pharmaceutical tools recognized by the Pharmacopoeias. Examples which may be mentioned for the preparation of pharmaceutical forms intended for the oral route are: starch, magnesium stearate, talc, gelatin, agar, pectin, lactose, polyethylene glycols, etc. The pharmaceutical forms which can be used will be chosen from the following possibilities: splittable or non-splittable tablets, gel capsules, lozenges, granules, powders. According to the characteristics of the pathology to be treated and the morphology of each patient, the daily oral dose will be between 0.02 and 50 mg/kg/day taken in 1 to 3 doses uniformly spaced in order to maintain an effective level of occupation of the platelet GpIIb/IIIa receptors. Via the intravenous route, the pharmaceutical forms intended for the acute phase of the treatment are designed so as to allow an individual dosage adaptation on the basis of the inhibition of platelet aggregation which is most efficient as a function of the immediate evolution of the operation follow-ups. In this context, the lyophilizate and the ready-to-use solution for infusion make it possible to individually modify the dosage within the dosage range 0.01 mg/kg/day–20 mg/kg/day.

What is claimed is:

1. Compounds of general formula (I):

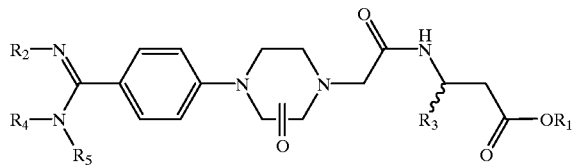

(I)

in which:
- $R_1$ is chosen from hydrogen, a $C_1$–$C_4$ alkyl group and a phenyl ($C_1$–$C_4$ alkyl) group;
- $R_2$ is chosen from hydrogen, a hydroxyl group, ethoxycarbonyl, benzyloxycarbonyl, p-nitrobenzyloxycarbonyl and t-butoxycarbonyl;
- $R_3$ is chosen from
    - $C_1$–$C_5$ alkyl, $C_3$–$C_{12}$ mono- or bicyclic cycloalkyl, $C_2$–$C_4$ alkenyl and $C_2$–$C_4$ alkynyl groups, these groups optionally being substituted with groups chosen from halogens and the hydroxyl group;
    - mono-, bi- or tricyclic $C_6$–$C_{14}$ aryl groups,
    - heteroaryl groups chosen from pyridyl, thienyl, furyl, quinolyl, benzodioxanyl, benzodioxolyl, benzothienyl, benzofuryl and pyrazinyl;
    - phenyl ($C_1$–$C_4$) alkyl and napthyl ($C_1$–$C_4$) alkyl groups optionally substituted on the aryl nucleus, and piperonyl,
- $R_4$ and $R_5$ are chosen independently of each other, from hydrogen and a $C_1$–$C_5$ alkyl group, or form, together with the nitrogen atom, a group chosen from piperidyl and morpholinyl,
- aryl and heteroaryl groups optionally being substituted with one or more groups chosen independently from halogens, $C_1$–$C_4$ alkyl, trifluoromethyl, $C_1$–$C_4$ alkylthio, $C_1$–$C_4$ alkylsulphonyl, $C_1$–$C_4$ alkyloxy, nitro and groups —COOR, —CH$_2$COOR and —O—CH$_2$—COOR, R being a $C_1$–$C_4$ alkyl group,
- and the oxo group is in position 2 or 3 on the piperazine; and the addition salts thereof with pharmaceutically acceptable acids.

2. Compounds according to claim 1, which are chosen from ethyl 3-{[2-(4-{4-[amino(hydroxyimino)methyl]phenyl}-2-oxopiperazino)acetyl]amino}-3-(1,3-benzodioxol-5-yl)propanoate, ethyl 3-{[2-(4-{4-[amino(hydroxy-imino)methyl]phenyl}-2-oxopiperazino)acetyl]amino}-5-phenylpentanoate, 3-{[2-(4-{4-[amino(imino)methyl]-phenyl}-2-oxopiperazino)acetyl]amino}-3-(1,3-benzodioxol-5-yl)propanoic acid and the addition salts thereof with pharmaceutically acceptable acids.

3. Compounds of general formula (I):

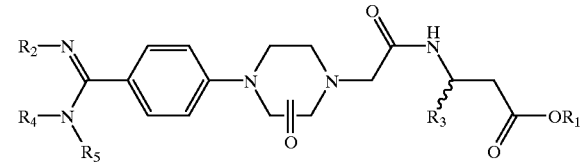

(I)

in which:
- $R_1$ is chosen from hydrogen, a $C_1$–$C_4$ alkyl group and a phenyl ($C_1$–$C_4$ alkyl) group;
- $R_2$ is chosen from hydrogen, a hydroxyl group, ethoxycarbonyl, benzyloxycarbonyl, p-nitrobenzyloxycarbonyl and t-butoxycarbonyl;
- $R_3$ is chosen from
    - mono-, bi- or tricyclic $C_6$–$C_{14}$ aryl groups,
    - heteroaryl groups chosen from pyridyl, thienyl, furyl, quinolyl, benzodioxanyl, benzodioxolyl, benzothienyl, benzofuryl and pyrazinyl;
    - phenyl ($C_1$–$C_4$) alkyl and napthyl ($C_1$–$C_4$) alkyl groups optionally substituted on the aryl nucleus, and piperonyl,
- $R_4$ and $R_5$ are chosen independently of each other, from hydrogen and a $C_1$–$C_5$ alkyl group, or form, together with the nitrogen atom, a group chosen from piperidyl and morpholinyl,
- aryl and heteroaryl groups optionally being substituted with one or more groups chosen independently from halogens, $C_1$–$C_4$ alkyl, trifluoromethyl, $C_1$–$C_4$ alkylthio, $C_1$–$C_4$ alkylsulphonyl, $C_1$–$C_4$ alkyloxy, nitro and groups —COOR, —CH$_2$COOR and —O—CH$_2$—COOR, R being a $C_1$–$C_4$ alkyl group,
- and the oxo group is in position 2 or 3 on the piperazine; and the addition salts thereof with pharmaceutically acceptable acids.

4. Process for preparing the compounds of formula I according to claim 1, by a) reacting an acid of formula

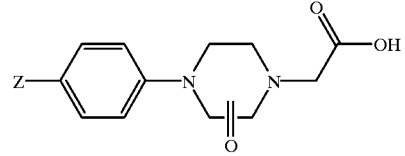

(II)

in which Z is a precursor group of a group

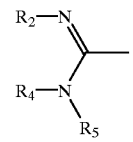

with an amine of formula

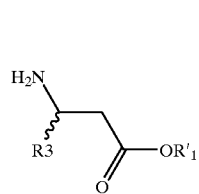

in which $R'_1$ is a $C_1-C_4$ alkyl or phenyl($C_1-C_4$ alkyl) group, to give a compound of formula

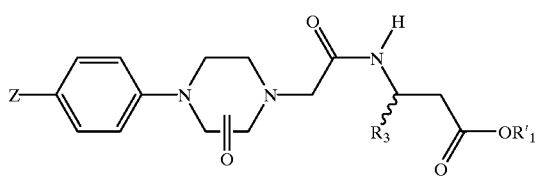

b) converting the group Z into a group

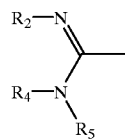

and c) optionally, converting the group $R'_1$ into a hydrogen atom.

5. Antithrombotic composition which comprises an effective amount of a compound as defined in claim 1, in admixture with a pharmaceutically acceptable excipient.

6. Process for treating a thrombosis in a patient, comprising the administration to this patient of an effective amount of a compound according to claim 1.

7. Process for preventing the risk of thrombosis in a patient, comprising the administration to this patient of an effective amount of a compound according to claim 1.

* * * * *